US006455031B1

(12) United States Patent
Davies et al.

(10) Patent No.: US 6,455,031 B1
(45) Date of Patent: *Sep. 24, 2002

(54) METHODS AND COMPOSITIONS FOR CONTROLLING BIOFILM DEVELOPMENT

(76) Inventors: David G Davies, 703 S. 11th Ave., Bozeman, MT (US) 59715; John W Costerton, 1206 Brentwood Ave., Bozeman, MT (US) 59718

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,580
(22) PCT Filed: Jun. 18, 1998
(86) PCT No.: PCT/US98/12695
§ 371 (c)(1),
(2), (4) Date: Jun. 9, 1999
(87) PCT Pub. No.: WO98/57618
PCT Pub. Date: Dec. 23, 1998

Related U.S. Application Data
(60) Provisional application No. 60/050,093, filed on Jun. 18, 1997.

(51) Int. Cl.$^7$ .............................. A61K 7/22; A61K 7/24
(52) U.S. Cl. ........................... 424/54; 424/55; 435/375; 549/321
(58) Field of Search ......................... 549/321; 435/375; 424/54, 55

(56) References Cited

U.S. PATENT DOCUMENTS

| | | | |
|---|---|---|---|
| 4,650,750 A | | 3/1987 | Giese |
| 4,709,016 A | | 11/1987 | Giese |
| 5,239,088 A | | 8/1993 | Hoffman et al. |
| 5,320,805 A | | 6/1994 | Kramer et al. |
| 5,536,750 A | | 7/1996 | deSolms et al. |
| 5,591,872 A | * | 1/1997 | Pearson et al. ............. 549/321 |
| 5,593,827 A | | 1/1997 | Bycroft et al. |
| 5,686,472 A | | 11/1997 | Anthony et al. |
| 5,776,974 A | | 7/1998 | Bycroft et al. |
| 6,337,347 B1 | | 1/2002 | Livinghouse |

FOREIGN PATENT DOCUMENTS

| | | |
|---|---|---|
| JP | 58096079 A | 6/1983 |
| JP | 60045568 A | 3/1985 |
| WO | WO 92/18614 | 10/1992 |
| WO | WO 96/29392 | 9/1996 |
| WO | WO 97/27851 | 8/1997 |

OTHER PUBLICATIONS

Bainton, N.J. et al., "A general role for the *lux* autoinducer in bacterial cell signalling: control of antibiotic biosynthesis in *Erwinia*," Gene, 1992, vol. 116, 87–91.

Bainton, N.J. et al., "N-(3-Oxohexanoyl)-L-homoserine lactose regulates carbapenem antibiotic production in *Erwinia carotovora*", Biochemistry Journal, 1992, vol. 288, 997–1004.

Bever, R. A. et al., "Molecular Characterization and Nucleotide Sequence of the *Pseudomas aeruginosa* Elastase Structural Gene", Journal of Bacteriology, 1988, vol. 170, No. 9, 4309–4314.

Cao, J–G. et al., "Biosynthesis and Stereochemistry of the Autoinducer Controlling Luminescence in *Vibrio harveyi*", Journal of Bacteriology, 1993, vol. 175, No. 12, 3856–3862.

Cao, J–G. et al., "Purification and Structural Identification of an Autoinducer for the Luminescence System of *Vibrio harveyi*", Journal of Biological Chemistry, 1989, vol. 264, No. 36, 21670–21676.

Choi, S.H. et al., "Genetic Dissection of DNA Binding and Luminescence Gene Activation by the *Vibrio fischeri* LuxR Protein", Journal of Bacteriology, 1992, vol. 174, No. 12, 4064–4069.

Eberhard, A. et al., "Analogs of the autoinducer of bioluminescence in *Vibrio fischeri*", Archives of Microbiology, 1986, vol. 146, No. 35, 35–40.

Eberhard, A. et al., "Structure Identification of Autoinducer of *Photobacterium fischeri* Luciferase", Biochemistry, 1981, vol. 20, 2444–2449.

Eberhard, A. et al., "Synthesis fo the *lux* gene autoinducer in *Vibrio fischeri* is positively autoregulated", Archives of Microbiology, 1991, vol. 155, 294–297.

Gambello, M.J. and Iglewski, "Cloning and Characterization of the *Pseudomonas aeruginosa lasR* Gene, a Transcriptional Activator of Elastase Expression", Journal of Bacteriology, 1991, vol. 173, No. 9, 3000–3009.

Goswami, A. et al., "Microbial Hydroxylation of Quadrone to 8a–Hydroxyquadrone", Journal of Natural Products, 1987, vol. 50, No. 1, 49–54.

Hoiby, N. "*Pseudomonas Aeruginosa* Infection in Cystic Fibrosis", Acta. Path. Microbiol. Scand. Sect. B., 1974, vol. 82, 551–558.

Iglewski, B.H. and Kabat, D. "NAD–Dependent Inhibition of Protein Synthesis by *Pseudomonas aeruginosa* Toxin", PNAS USA 1975, vol. 72, 2284–2288.

Iglewski, B.H. et al., "*Pseudomonas aeruginosa* exoenzyme S: An adenosine diphosphate ribosyltransferase distinct from toxin A", PNAS USA 1978, vol. 75, No. 7, 3211–3215.

Jones, S. et al., "The *lux* autoinducer regulates the production of exoenzyme virulence in *Erwinia carotovora* and *Pseudomonas aeruginosa*", EMBO Journal, 1993, vol. 12, No. 6, 2477–2482.

(List continued on next page.)

Primary Examiner—James Ketter
(74) Attorney, Agent, or Firm—Lahive & Cockfield, LLP; Peter C. Lauro, Esq.; Elizabeth A. Hanley, Esq

(57) ABSTRACT

A method of cleaning or protecting surfaces by treatment with compositions comprising N-(3-oxododecanoyl)-L-homoserine lactone (OdDHL) blocking compounds and/or N-butyryl-L-homoserine lactone (BHL) analogs, either in combination or separately.

32 Claims, 5 Drawing Sheets

OTHER PUBLICATIONS

Kaplan, H.B. and Greenberg, E.P. "Diffusion of Autoinducer Is Involved in Regulation of the *Vibrio fischeri* Luminescence System", *Journal of Bacteriology*, 1985, vol. 163, 1210–1214.

Kessler, E. and Safrin, M. "Synthesis, Processing and Transport of *Pseudomonas aeruginosa Elastase*", *Journal of Bacteriology*, 1988, vol. 170, No. 11, 5241–5247.

Meighen, E.A. "Molecular Biology of Bacterial Bioluminescence", *Microbiological Reviews*, 1991, vol. 55, No. 1, 123–142.

Nicas T.I. and Iglewski, B.H. "The Contribution of exoproducts to virulence of *Pseudomonas aeruginosa*", *Canadian Journal of Microbiology*, 1985, vol. 31, No. 4, 387–392.

Passador, L. et al., "Expression of *Pseudomas aeruginosa* Virulence Genes Requires Cell–to–Cell Communication", *Science*, 1993, vol. 260, 1127–1130.

Passador, L. et al., "Functional analysis of the pseudomonas aeruginosa autoinducer PAI"., *J. Bacteriology*, 1996, 5990–6000.

Pearson, J.P. et al., "Structure of the autoinducer required for expression of *Pseudomonas aeruginosa* virulence genes", *PNAS USA*, 1994, vol. 91, No. 1, 197–201.

Piper, K.R. et al., "Conjugation factor of *Agrobacterium tumefaciens* regulates Ti plasmid transfer by autoinduction", *Nature*, 1993, vol. 362, 448–450.

Pirhonen, M. et al., "A small diffusible signal molecule is responsible for the global control of virulence and exoenzyme production in the plant pathogen *Erwinia carotovora*", *EMBO Journal*, 1993, vol. 12, No. 6, 2467–2476.

Ralling, G. et al., "Growth rate–dependent regulation of RNA polymerase synthesis in *Escherichia coli*", *Mol. Gen. Genet.*, 1985, vol. 201, 379–386.

Reynolds, H.Y. et al., "*Pseudomonas aeruginosa* Infections: Persisting Problems and Current Research to Find New Therapies", *Annals of Internal Medicine*, 1975, vol. 82, No. 6, 819–831.

Robson et al., "Bacterial N–acyl–homoserine–lactone–dependent signaling and its potential biotechnological applications", *Trends in Biotechnol.* 1997, vol. 15, 458–464.

Stewart, G.S.A.B. and Williams, P., "Shedding New Light On Food Microbiology", *ASM News*, 1993, vol. 59, No. 5, 241–247.

Wierenga, W. and Skulnick, H.I. "General, Efficient, One–Step Synthesis of α–Keto Esters", *Journal of Organic Chemistry*, 1979, vol. 44, No. 2, 310–311.

Williams, et al., "Small molecule–mediated density–dependent control of gene expression in pro–karyotes: Bioluminescence and the biosynthesis of carbapenem antibiotics", *FEMS Microbiol*, 1992, vol. 100, 161–168.

Zhang, L. et al., "*Agrobacterium* conjugation and gene regulation by N–acyl–L–homoserine lactones", *Nature*, 1993, vol. 362, 446–448.

Database Medline Express, US National Library of Medicine, No. 9730387, Reimann et al., "The global activator GacA of pseudomonas aeruginosa PAO positively controls the production of the autoinducer N–butyryl–homoserine lactone and the formation of the virulence factors pyocyanin, cyanide, and lipase", abstr., *Mol. Microbiol.* 1997 vol. 24 No. 2, 309–319.

Allison, D.G. et al., "A staining technique for attached bacteria and its correlation to extracellular carbohydrate production", *J. Microbiol. Methods*, 2:93–99 (1984).

Allison, D.G. et al., "The role of polysaccharides in adhesion of freshwater bacteria", *J. Gen. Microbiol.*, 133:1319–1327 (1987).

Anwar, H. et al., "Dynamic interactions of biofilms on mucoid pseudomonas aeruginosa with tobramycin and piperacillin", *Antimicrob. Agents Chemother.*, 36:1208–1214 (1992).

Bainton, N.J. et al., "A general role for the lux autoinducer in bacterial cell signalling: Control of antibiotic synthesis in Erwina", *Gene.*, 116:87–91 (1992).

Bainton, N.J. et al., "N–(3–oxohexaoyl)–1–homoserine lactone regulates carbepenem antibiotic production in Erwina carotovora", *Biochem. J.*, 288:997–1004 (1992).

Beck von, B.S. et al., "Capsular polysaccharide biosynthesis and pathogenicity in Erwina carotovora", *J. Bacteriol.*, 177:5000–5008 (1995).

Boivin, J. et al., Biofilms and biodeterioration. In Biodeterioration and biodegradation 8 (ed.) H.W. Rossmore, *Elsevier Applied Science*, London, pp. 53–62 (1991).

Boyd, A. et al., "Sequence of the algL gene of pseudomonas aeruginosa and purification of its alginate lyase product", *Gene*, 131:1–8 (1993).

Boyd, A. et al., "Role of the alginate lyase in cell attachment of pseudomonas aeruginosa", *Appl. Environ. Microbiol.*, 60:2325–2359 (1994).

Brint, J.M. et al., "Synthesis of mulitple exoproducts in pseudomonas aeruginosa is under the control of RH1R–Rh1l. Another set of regulators in strain PAO1 with homology to the autoinducer–responsive LuxR–Luxl family", *J. Bacteriol.*, 177:7155–7163 (1995).

Christensen, B.E. et al., "Physical and chemical properties of biofilms", *In*: Characklis, W.G. et al (eds.) Biofilms. John Wiley & Sons, New York, pp. 93–130 (1990).

Cohen–Bazire, G. et al., "Kinetic studies of pigment synthesis by non–sulfur purple bacteria", *J. cell. Comp. Physiol.*, 49:25–68 (1957).

Costerton, J.W. et al., "Bacteriol biofilms in nature and disease", *Ann. Rev. Microbiol.*, 41:435–464 (1987).

Davies, D.G. et al., "Exopolysaccharide production in biofilms. Substratum activation of alginate gene expression by pseudomonas aeruginosa", *Appl. Environ. Microbiol.*, 59:1181–1186 (1993).

Davies, D.G. et al., "Regulation of the alginate biosynthesis gene algC in pseudomonas aeruginosa during biofilm development in continuous culture", *Appl. Environ. Microbiol.*, 61:860–867 (1995).

Dempsey, M.J., "Marine bacterial fouling: A scanning electron microscope study", *Marine Biol.*, 61:305–315 (1981).

Eberhard, A. et al., "Structural identification of autoinducer of photobacterium fischeri luciferase", *Biochemistry*, 20:2444–2449 (1981).

Eberhard, A. et al., "Anologs of the autoinducer of bioluminescence in vibrio fischeri", *Arch. Microbiol.*, 146:35–40 (1986).

Finlay, B.B. et al., "Common themes in microbial pathogenicity", *Microbiol. Rev.*, 53:210–230 (1989).

Fletcher, M. "Adherence of marine micro–organisms to smooth surfaces", pp. 347–371. *In* Beachey, E.H. (ed.), Bacterial Adherence (*receptors and recognition, series 3 vol. 6.*) Chapman & Hall, London (1980).

Floodgate, G.D. "The mechanism of bacterial attachment to detritus in aquatic systems", Memorie dell 'Istituto Italiano di idrobiologica Dott. Carco di Marchi 29 (suppl.), 309–323 (1972).

Fuqua, W.C. et al. "Quorum sensing in bacteria: The luxR–luxI family of cell desity–responsive transcriptional regulators", *J. Bacteriol.*, 176:269–275 (1994).

Gacesa, P., "Alginate–modifying–enzymes. A proposed unified mechanism of action for the lyases and epimerases", *FEBS Lett.*, 212:199–202 (1987).

Gambello, M.J. et al., "LasR of pseudomonas aeruginosa is a transcriptional activator of the alkaline protease gene (apr) and an enhancer of exotoxin A expression", *Infect. Immun.*, 61:1180–1184 (1993).

Geesey, G.G. et al., "Microscopic examination of natural sessile bacterial populations from Alpine streams", *Can. J. Microbiol.*, 23:1733–1736 (1997).

Givskov, M. et al., "Eukaryotic interference with homoserine lactone–mediated prokaryotic signalling", *J. Bacteriol.*, 178:6618–6622 (1996).

Holloway, B.W., "Genetic recombination in pseudomonas aeruginosa", *J. Gen. Microbiol.*, 13:572–581 (1955).

Hengge–Atonis, R., "Survival of hunger and stress: The role of rpoS in early stationary phase regulation in escherichia Coli", *Cell*, 72:165–168 (1993).

Jones, H.C. et al., "Electron microscopic study of a slime layer", *J. Bacteriol*, 99:316–325 (1969).

Kaplan, H.B. et al., "Diffusion of autoinducer is involved in regulation of the vibrio fischeri luminescence system", *J. Bacteriol.*, 163:1210–1214 (1985).

Khoury, A.E. et al., "Prevention and control of bacterial infections associated with medical devices", *ASAIO J.*, 38:174–178 (1992).

Kintner, P.K.III, et al., "Carbohydrate interference and its correction in pectin analysis using the m–hydroxydiphenyl method", *J. Food Sci.*, 47:756–760 (1982).

Latifi, A. et al., "Multiple homologues of luxR and luxI control expression of virulence determinants and secondary metabolites through quorum sensing in pseudomonas aeruginosa PAO1", *Mol. Microbiol.*, 17:333–344 (1995).

Latifi, A. et al., "A hierarchical quorum sensing cascade in pseudomonas aeruginosa links the transcriptional activators lasR and Rh1R (VsmR) to expression of the stationary–phase sigma factor RpoS", *Mol. Microbiol.*, 21:1137–1146 (1996).

Nicholas, W.W. et al., "The penetration of antibiotics into agregates of mucoid and nonmucoid pseudomonas aeruginosa", *J. Gen. Microbiol.*, 135:1291–1303 (1989).

Ochsner, U.A., et al., "Autoinducer–mediated regulation of rhamnolipid biosurfactant synthesis in pseudomonas aeruginosa", *PNAS USA*, 92:6424–6428 (1995).

Pearson, J.P. et al., "Structure of the autoinducer required for expression of pseudomonas aeruginosa virulence genes", *PNAS USA*, 91:197–201 (1994).

Pearson, J.P. et al., "A second N–acylhomoserine lactone signal produced by pseudomonas", *PNAS USA*, 92:1490–1494 (1995).

Peterson, G.L., "A simplification of the protein assay method of Lowry et al. Which is more generally applicable", *Anal. Biochem.*, 83:346–356 (1997).

Preiss, J. et al., "Alginic acid metabolism in bacteria. I. enzymatic formation of unsaturated oligosaccharides and I–deoxy–L–erythro–5–hexoseulose uronic acid", *J. Biol. Chem.*, 237:309–316 (1962).

Schiller, N.L. et al., "Characterization of the Pseudomonas aeruginosa alginate lyase gene (algL): cloning, sequencing and expression in Escherichia coli", *J. Bacteriol.* 175:4780–4789 (19930).

Schripsema, J. et al., "Bacteriocin small of Rhizobium leguminosarum belongs to the class of N–acyl–L–homoserine Lactone molecules, known as autoinducers and as quorum sensing co–transcription factors", *J. Bacteriol.* 178:366–371 (1996).

Stewart, P.S., "Biofilm accumulation model that predicts antibiotic resistance of Pseudomonas aeruginosa biofilms", *Antimicrob. Agents Chemother*. 38:1052–1058 (1994).

Srinivasan, R. et al., "Biofilm parameters influencing biocide efficacy", *Biotech. Bioeng*. 46:553–560 (1995).

Sutherland, I.W. "Polysaccharides in the adhesion of marine and freshwater bacteria," pp. 329–338 *In* R.C. W. Berkeley, et al. (eds.), Microbial Adhesion to Surfaces. Ellis Horwood, London (1980).

Swift, S. et al., "A novel strategy for the insolation of *lux/homologues* evidence for the widespread distribution of a LuxR:Lux1 superfamily in enteric bacteria", *Mol. Microbiol.* 10:511–520 (1993).

Tashiro, H. et al., "Penetration of biocides into biofilms", *Wat. Sci. Technol.* 23:1395–1403 (1991).

Throup, J. et al., "Characterization of the *yenlyenR* locus from Yersinia enterocolitica mediating the synthesis fo the N–acylhomoserine lactone signal molecules", *Mol. Microbio.*, 17:345–356 (1995).

Wallace, W.H. et al., "An algD–Bioluminescent reporter plasmid to monitor algimate production in biofilms", *Microb. Ecol.* 27:225–239 (1994).

Wardell, J.N. et al., *In* Microbes and surfaces. Symposia for the Society for General Microbiology. 34:351–378 (1983).

Winson, M.K. et al., "Multiple N–acyl–L–homoserine lactone signal molecules regulate production of virulence determinants and secondary metabolites in Pseudomonas aeruginos", *Proc. Natl. Acad. Sci. USA*. 92:9427–9431 (1995).

Zhang, L. et al., "Agrobacterium conjugation and gene regulation by N–acyl–J–homoserine lactones", *Nature*. 362:446–448 (1993).

Zobell, C.E., "The effect of solid surfaces upon bacterial activity", *J. Bacteriol*. 46:39–56 (1943).

U.S. application No. 09/591,476, Davies et al., filed Jun. 9, 2000.

U.S. applicaton No. 09/969,501, Livinghouse, filed Oct. 1, 2001.

* cited by examiner

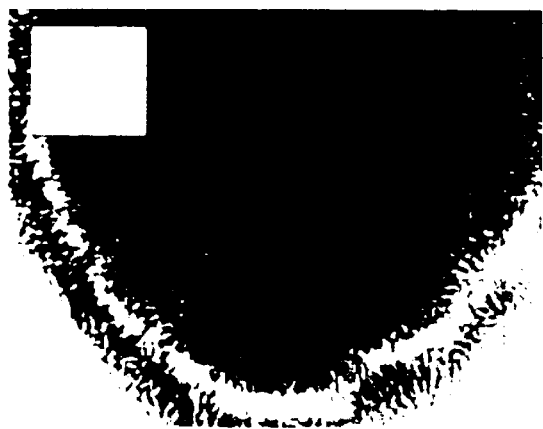
FIG.2A
FIG.2B
FIG.2C
FIG.2D
a: JP1 cell cluster at time of 0.2% SDS addition
b: cell cluster 20 min. post SDS addition
c: cell cluster 25 min. post SDS addition
d: cell cluster 30 min. post SDS addition

METHODS AND COMPOSITIONS FOR CONTROLLING BIOFILM DEVELOPMENT

CROSS-REFERENCE TO RELATED APPLICATION

This application claims the benefit of the filing date of Provisional Application No. 60/050,093, filed Jun. 18, 1997.

STATEMENT REGARDING FEDERALLY SPONSORED RESEARCH OR DEVELOPMENT

Not applicable.

TECHNICAL FIELD

This invention relates to certain homoserine lactone compositions and methods for their use in biofilm regulation.

BACKGROUND OF THE INVENTION

Biofilms are biological films that develop and persist at interfaces in aqueous environments (Geesey, et al., Can. J. Microbiol. 32. 1733–6, 1977; 1994; Boivin and Costerton, Elsevier Appl. Sci., London, 53–62, 1991; Khoury, et al., ASAIO, 38, M174–178, 1992; Costerton, et al., J. Bacteriol., 176, 2137–2142, 1994), especially along the inner walls of conduit material in industrial facilities, in household plumbing systems, on medical implants, or as foci of chronic infections. These biological films are composed of microorganisms embedded in an organic gelatinous structure composed of one or more matrix polymers which are secreted by the resident microorganisms. Biofilms can develop into macroscopic structures several millimeters or centimeters in thickness and can cover large surface areas. These biological formations can play a role in restricting or entirely blocking flow in plumbing systems and often decrease the life of materials through corrosive action mediated by the embedded bacteria. Biofilms are also capable of trapping nutrients and particulates that can contribute to their enhanced development and stability.

The involvement of extracellular polymers in bacterial biofilms has been documented for both aquatic (Jones, et al., J. Bacteriol., 99, 316–325, 1969; and marine bacteria (Floodgate, Memorie dell'Instituto italiano di idrobiologica Dott. Carco di Marchi 29 (suppl.), 309–323 1972), and the association of exopolysaccharides with attached bacteria has been demonstrated using electron microscopy (Geesey, et al., supra; Dempsey, Marine Biol. 61, 305–315, 1981) and light microscopy (Zobell, J. Bacteriol. 46, 39–56, 1943. The presence of such exopolysaccharides is believed to be involved in the development of the microbial biofilm (Allison and Sutherland, J. Microbiol. Methods, 2, 93–99, 1987). Analysis of biofilm bacteria isolated from freshwater and marine environments has shown that the polymers they produce are composed largely of acidic polysaccharides. The control and removal of biofilm material from pipe and conduit surfaces has historically been carried out by the addition of corrosive chemicals such as chlorine or strong alkali solutions or through mechanical means. Such treatments are generally harsh to both the plumbing systems and the environment, and have been necessary due to the recalcitrant nature of biofilms within those systems. The resistance to treatment by biocides has been due in large measure to the protective character of intact biofilm matrix polymers (Srinivasan, et al., Biotech. Bioeng., 46, 553–560, 1995.

Modern methods of direct observation of living biofilms have established the very complicated structural architecture (Costerton, et al., Ann., Rev. Microbiol., 49, 711–745, 1995) of these sessile microbial populations. The overriding structural element responsible for development and maintenance of this biofilm architecture is the matrix polymer that is produced by the resident microorganisms. That populations of associated bacteria could produce structures as complex as are found in biofilms suggested the operation of a cell-cell signaling mechanism.

Prior to 1981, microbiologists had generally assumed that bacteria had neither the requirement nor the capability of producing cell-cell signaling molecules. In 1981, it was shown by Eberhard, et al. Biochemistry, 20, 2444–2499, 1981, that the bacterium *Photobacterium fischeri* produces a compound 3-oxo-N-(tetrahydro-2-oxo-3-furanyl) hexanamide, also known as vibrio (photobacterium) autoinducer (VAI), which is associated with bacterial luminescence under conditions of high cell density. The cell membrane of *P. fischeri* was shown to be permeable to VAI by Kaplan and Greenberg in 1985 (J. Bacteriol., 163, 1210–1214, 1985). At low bacterial cell densities in broth medium, VAI passively diffuses out of the cells along a concentration gradient, where it accumulates in the surrounding medium. At high cell densities the concentration of VAI outside the cells is equivalent to the concentration of VAI inside the cells. Under such conditions VAI was shown to initiate transcription of luminescence genes. Using such a system, bacteria are able to monitor their own population density and regulate the activity of specific genes at the population level.

For several years it was presumed that the autoinducer involved in bacterial luminescence was unique to the few bacteria that produce light in the marine environment. Then, in 1992, the terrestrial bacterium Erwinia carotovora was shown to use an autoinducer system to regulate the production of the β-lactam antibiotic carbapenem (Bainton, et al., Biochem J., 288, 297–1004, 1992b). The molecule found to be responsible for autoinduction of carbapenem was shown to be an acylated homoserine lactone (HSL), a member of the same class of molecule responsible for autoinduction in bioluminescence. This finding led to a general search for HSLs in a wide range of bacteria. To affect the search, a bioluminescence sensor system was developed and used to screen for HSL production in the spent supernatant liquids of a number of bacterial cultures. Many different organisms were shown by the screening to produce HSLs. These included: *Pseudomonas aeruginosa, Serratia marcescens, Erwinia herbicola, Citrobacter freundii, Enterobacter agglomerans* and *Proteus mirabilis* (Brainton, et al., Gene. 116, 87–91, 1992a; Swift, et al., Mol. Microbiol., 10, 511–520, 1993). More recently, the list has grown to include *Erwinia stewartii* (Beck, J. Bacteriol, 177, 5000–5008, 1993), *Yersinia enterocolitica* (Throup, et al., Mol. Microbiol., 17, 345–356, 1995), *Agrobacterium tumefaciens* (Zhang, et al., Nature, 362, 446–448, 1993), *Chromobacterium violaceum* (Winston, et al., Proc. Natl. Acad. Sci., USA, 92, 9427–9431, 1995), *Rhizobium leguminosarium* (Schripsema, et al., J. Bacteriol, 178, 366–371 1996) and others. Today it is generally assumed that all enteric bacteria, and the gram negative bacteria generally, are capable of cell density regulation using HSL autoinducers.

In 1993 Gambello, et al. Infect. Immun., 61, 1880–1184, (1993) showed that the α-HSL product of the LasI gene of *Pseudomonas aeruginosa* controls the production of exotoxin A, and of other virulence factors, in a cell density dependent manner. Since that time, the production of a large number of Pseudomonas virulence factors have been shown to be controlled by α-HSL compounds produced by the LasI and RhlI regulatory systems (Ochsner, et al., Proc. Natl.

Acad. Sci., USA 92, 6424–6428, 1995; Winson, et al., supra; Latifi, et al., 1995), in a manner reminiscent of the Lux system. Latifi, et al. Mol. Microbiol, 21, 1173–1146, (1996) have also shown that many stationary phase properties of *P. aeruginosa*, including those controlled by the stationary phase sigma factor (RpoS), are under the hierarchical control of the LasI and RhlI cell-cell signaling systems.

In all cases, homoserine lactone autoinducers are known to bind to a DNA binding protein homologous to LuxR in *Photobacterium fischeri*, causing a conformational change in the protein initiating transcriptional activation. This process couples the expression of specific genes to bacterial cell density (Latifi, et al. supra, 1996). Regulation of this type has been called 'quorum sensing' because it suggests the requirement for a 'quorate' population of bacterial cells prior to activation of the target genes (Fuqua, et al., J. Bacteriol., 176, 269–275, 1994b). Expression of certain of these 'virulence factors' has been correlated with bacterial cell density (Finley and Falkow, Microbiol. Rev. 53, 210–230, 1989).

In *P. aeruginosa*, quorum sensing has been shown to be involved in the regulation of a large number of exoproducts including elastase, alkaline protease, LasA protease, hemolysin, cyanide, pyocyanin and rhamnolipid (Gambello, et al., supra; Latifi, et al., supra; Winson, et al., supra; Ochsner, et al., 1995); but has never before been shown to be involved in biofilm formation. Most of these exoproducts are synthesized and exported maximally as *P. aeruginosa* enters stationary phase.

The concept of cell signalling and quorum sensing has been studied in the art. See for example U.S. Pat. No. 5,591,872, to Pearson et al; Passador et al, Journal of Bacteriology, pages 5990–6000, October, 1996; PCT WO92/18614 and U.S. Pat. No. 5,593,827.

However, none of these prior publications recognize how these principles may be applied to enable the regulation of biofilms according to this invention.

BRIEF SUMMARY OF THE INVENTION

It is accordingly one object of the present invention to provide compositions and methods for the regulation of biofilms.

A further object of the invention is to provide novel methods for regulation, i.e., inhibition, enhancement, dispersion, etc., by administration of a group of homoserine lactone blockers or analogs.

An even further object of the invention is to provide methods to control, enhance, stimulate, diminish, prevent, inhibit, detach, remove, clean, and/or disperse biofilm development by administration of a selected group of homoserine lactone blockers or analogs.

Other objects and advantages of the invention will become apparent to those skilled in the art as the description of the invention proceeds.

In satisfaction of the foregoing objects and advantages, the present invention provides compositions to control, enhance, stimulate, diminish, prevent, inhibit, detach, remove, clean, and/or disperse biofilms which comprises a composition having as its active ingredient one or more homoserine lactone blocker or analog compounds. Especially preferred blockers and/or analogs, are selected from those of the following formulae:

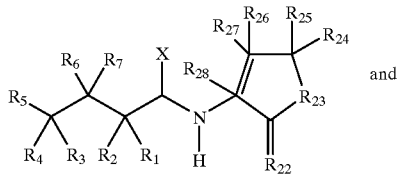

I

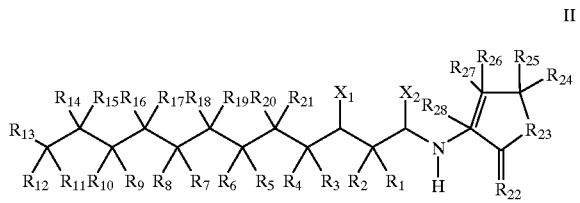

II wherein in the above formulae, $R_1$–$R_{21}$ are selected from H, $C_1$–$C_4$ alkyl group (preferably $CH_3$), OH, $NH_2$, SH or a halogen such as fluorine, chlorine bromine or iodine;

$R_{22}$ and $R_{23}$ are selected from S, O, and N—R, $R_{24}$–$R_{28}$ is H or a halogen, and X, $X_1$ and $X_2$ are selected from O, S, $H_2$ or any combination of H plus one halogen or two halogens when one or more R groups is substituted.

The present invention also provides methods to control, enhance, stimulate, diminish, prevent, inhibit, detach, remove, clean, and/or disperse biofilms, which method comprises administration of a composition of the invention. Included in such methods are methods to remove biofilm from surfaces to effect cleaning of the surfaces.

BRIEF DESCRIPTION OF THE FIGURES

Reference is now made to the drawings accompanying the application wherein:

FIGS. 2a, 2b, 2c, and 2d are cell cluster studies which show the effect of the addition of 0.2% SDS to a biofilm cell cluster of the lasI knockout strain *P. aerguginosa* PAO-JP1. The strain was grown in EPRI medium for 10 days in continuous culture reactor under flowing conditions (a). SDS was added to the culture reactor and flow was turned off for 30 min (b,c). Following incubation in the presence of SDS, flow was reinitiated (d);

DESCRIPTION OF THE INVENTION

Figure 1:
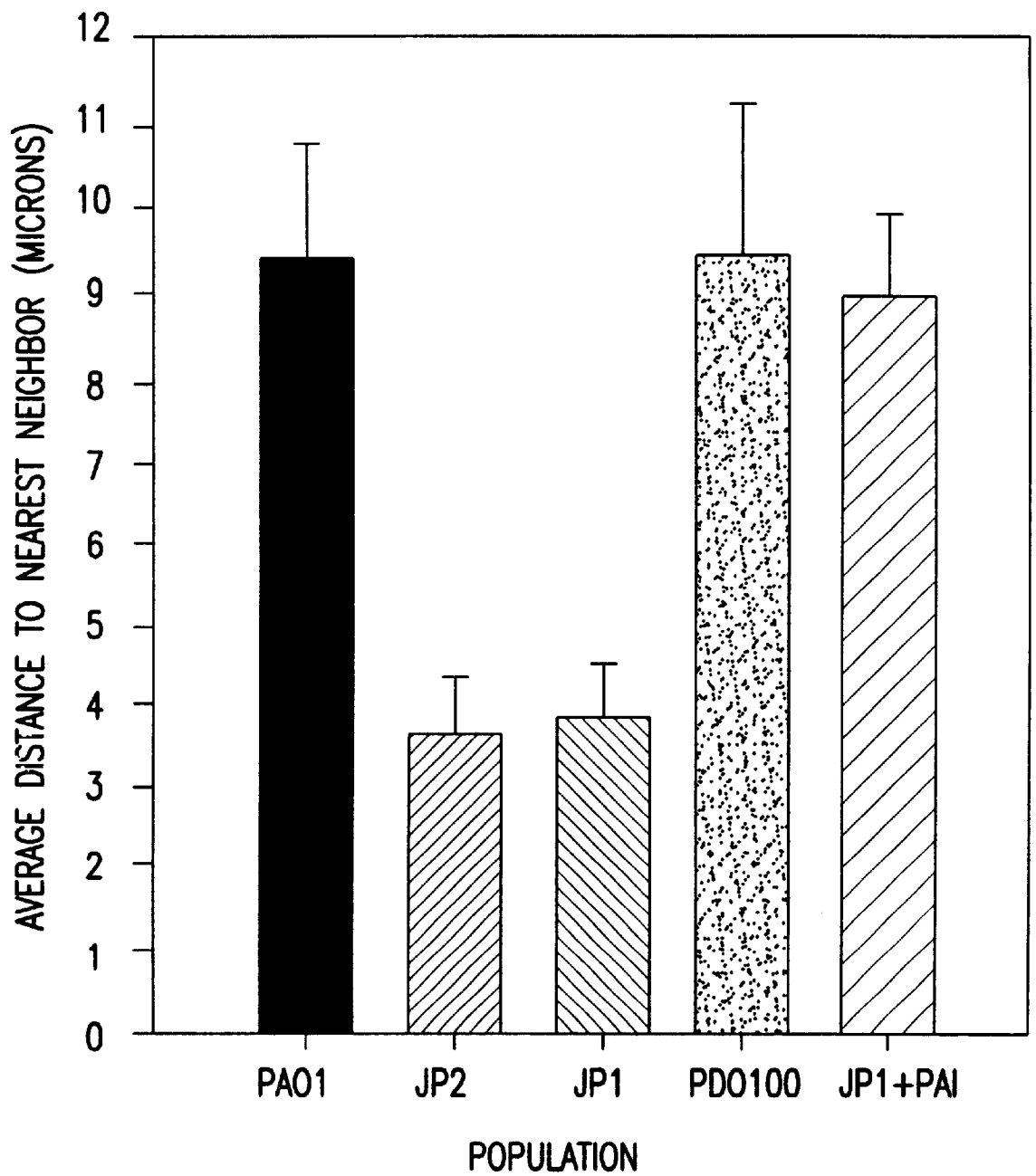
FIG. 1 is a "Neighbor Analysis" which shows the average distance between cells in biofilms composed of wild-type *P. aeruginosa* PAO1, the lasI/rhlI knockout mutant *P. aeruginosa* PAO-JP2, the LasI knockout *P. aeruginosa* PAO-JP1, the rhlI knockout *P. aeruginosa* PDO100 and *P. aeruginosa* JP1 grown in the presence of exogenous OdDHL N-(3-oxododecanoyl)-L-homoserine lactone (10 uM)

As noted above, the present invention provides compositions and methods for biofilm regulation as exemplified by biofilm removal from surfaces, for example hard and soft surfaces, woven and non-woven surfaces, and porous and non-porous surfaces. Other examples of surfaces which may be cleaned by removal of biofilm therefrom using the compositions of the invention include toilet bowls, bath tubs, drains, chairs, counter tops (such as those exposed to meats such as chicken), vegetables, meat processing rooms, butcher shops, airducts, air conditioners, carpets, paper or woven product treatment, diapers, healthy air machines, and in other areas as described herein.

The preferred compositions of the invention comprise active blocker or analog compounds selected from the group consisting of one or more compounds of the formulae:

N-Butyrl-L-Homoserine Lactone Analogs:

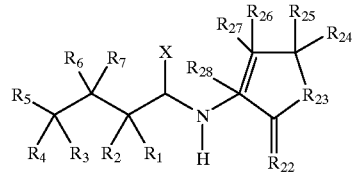

(I)

N(3-oxododecanoyl)-L-homoserine Lactone Blockers: II

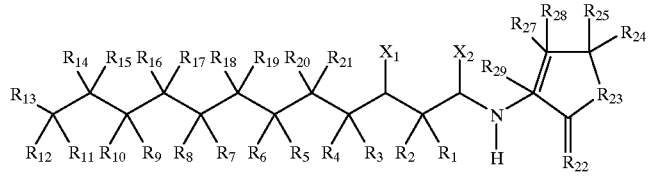

wherein in the above formulae $R_1$–$R_{21}$ are selected from H, $C_1$–$C_4$ alkyl group (preferably $CH_3$), OH, $NH_2$, SH or a halogen such as fluorine, chlorine bromine or iodine;

$R_{22}$ and $R_{23}$ are selected from S and O, $R_{24}$–$R_{28}$ is H or a halogen, and X, $X_1$ and $X_2$ are selected from O, S, $H_2$ or any combination of H plus one halogen or two halogens when one or more R groups is substituted.

The compounds of formulae (I) and (II) are fully disclosed and described in copending U.S. application Ser. No. 09/099,196 filed Jun. 18, 1998, the subject thereof being hereby incorporated herein by reference.

While the compositions and methods of the invention preferably employ active blocker and analog compounds as described herein, it should be understood that other active blockers and analogs may be used if they comply with the criteria described below.

The biofilm removing composition of this invention may be in the form of the active compound and a vehicle or carrier such as water or non-aqueous vehicle. Aqueous solutions or suspensions containing an effective amount of the active compound suitable to control, enhance, stimulate, diminish, prevent, inhibit, detach, disperse, remove and/or clean a biofilm on a surface, are preferred. The cleaning composition may also be in the form of a spray, a dispensable liquid, or a toilet tank drop-in or rim block for prevention and removal of soil and under-rim cleaning for toilets.

The methods of the present invention comprise administering a cleaning-effective amount of the active composition described above to a biofilm-containing surface. In another embodiment of the invention, the method comprises the step of administering a cleaning-effective amount of the composition to a surface which will prevent normal biofilm development.

As described herein, the discovery that cell communication molecules appear to be involved in biofilm development, has led to the present invention, and is the basis for the novel compositions and methods of the invention. At least two known N-acyl-L homoserine lactones appear responsible for the regulation of *Pseudomonas aeruginosa* biofilms; these are N-(3-oxododecanoyl)-L-homoserine lactone (OdDHL) and N-butyryl-L-homoserine lactone (BHL). The former has been demonstrated to regulate the development of *Pseudomonas aeruginosa* biofilms and to be responsible for maintaining the integrity of biofilm structures by controlling the production of biofilm matrix polymers. The latter has been shown to be involved in the dispersion of *Pseudomonas aeruginosa* biofilms, and regulating the production and release of molecules responsible for breaking down biofilm matrix material. These homoserine lactones have been isolated from a wide range of bacteria, and it is believed that they are also responsible for biofilm regulation in organisms other than *P. aeruginosa*.

By artificially manipulating the binding of homoserine lactones to their cognate receptor molecules, according to the present invention one can control the formation, development, persistence and dispersion of microbial biofilms. For instance, the addition of a blocking compound which blocks the binding of OdDHL to its cognate receptor (LasR) prevents the production of matrix polymer material as the bacteria continue to multiply. The result is that cell aggregates formed under these conditions can be easily dispersed by the addition of simple surfactants. Additionally, developed biofilms can be treated with an analog of the homoserine lactone BHL to induce the release of enzymes which can digest the biofilm matrix material and disperse the bacteria into the bulk medium. Such treatments can be used as an effective means of controlling biofilm ecology in nature and in cleaning applications.

The biofilm cleaning and removal compositions of the present invention comprise an active compound selected from the group consisting of OdDHL blocker compounds, and analogs of BHL, and especially one or more compounds of formula (I) or (II) described herein. By blocker compounds is meant a compound that will prevent native OdDHL from binding to its receptor protein (LasR). Blocker compounds could competitively bind to the OdDHL receptor or could bind to OdDHL itself to render it incapable of binding.

By analog is meant a compound that will mimic the activity of BHL. Most preferably, an analog of the present invention will bind to the BHL receptor in an irreversible manner.

Compounds which are blockers for OdDHL are functionally defined as any compound that interferes with normal biofilm development by interfering with the natural activity of OdDHL. Normal biofilm development is determined by measuring the following parameters in a microbial community at an interface: 1) Cell to cell distance, 2) Cell cluster thickness, 3) Alginate or other matrix polymer production, 4) Susceptibility to dispersion by surfactant. These parameters are defined more fully below under the heading: "Methods to verify the suitability of candidate compounds". Any compound which influences one or all of the above parameters by interfering with the activity of natural OdDHL shall be considered a blocking analog for OdDHL activity.

Compounds which are analogs of BHL are functionally defined as any compound that either mimics or enhances the natural activity of BHL as its function relates to biofilm dispersion. The natural activity of BHL is defined operationally as stimulating the release of enzymes from bacteria which are responsible for the breakdown of biofilm matrix polymers. This breakdown is measured by the reduction of biofilm extracellular polymers to smaller molecular weight fractions and/or by observable sloughing or dispersion of a biofilm following the release of such enzymes.

Due to the simple nature of the homoserine lactones as a group, analogs and blockers may be produced that can act on *P. aeruginosa* and other bacteria and microorganisms in general, particularly on pseudomonads and gram negative bacteria.

The two known homoserine lactones mentioned above are depicted below:

N-Butyryl-L-Homoserine Lactone(BHL)

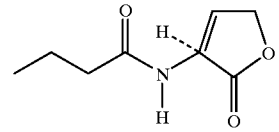

N(3-oxododecanoyl)-L-homoserine Lactone (OdDHL)

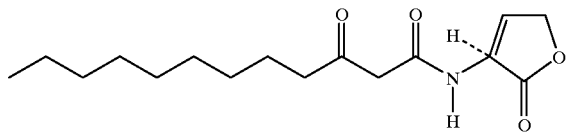

The preferred OdDHL blockers and BHL analogs of this invention are most preferably selected from the compounds disclosed below:

N-Butyryl-L-Homoserine Lactone analogs:

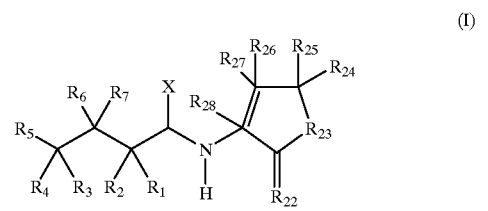

(I)

N(3-oxododecanoyl)-L-homoserine Lactone blockers:

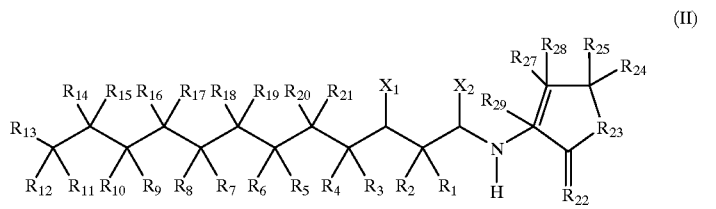

(II)

wherein, in the above formulae, $R_1-R_{21}$ are selected from H, $C_1-C_4$ alkyl group, (preferably ($CH_3$), OH, $NH_2$, SH or a halogen such as fluorine, chlorine bromine or iodine;

$R_{22}$ and $R_{23}$ are selected from S and O;

$R_{24}-R_{28}$ is H or a halogen; and

X, $X_1$ and $X_2$ are selected from O, S, $H_2$ or any combination of H plus one halogen or two halogens when one or more R group is substituted.

The preceding are preferred analog and blocker structures for homoserine lactones of the invention. A successful blocker will competitively bind to the cognate receptor protein (LasR) and block the binding of OdDHL, either inducing the receptor protein to bind to its receptor sites on the DNA molecule or preventing the receptor Protein from binding to its receptor sites on the DNA molecule.

These blockers and analogs may be modified without departing from the scope of the invention. Modifications may be as follows:

1) Alteration of the acyl side chain by increasing or decreasing its length.

2) Alteration of the structure of the acyl side chain, such as addition of a double bond or a triple bond between carbon atoms within the acyl side chain.

3) Substitution on carbons in the acyl side chain, e.g., the addition of a methyl group or other group such as an oxo-group, a hydroxyl group, an amino group, a sulfur atom, a halogen or dihalogen or some other atom or R-group to any location along the acyl side chain.

4) Substitution of carbons comprising the backbone of the acyl side chain with S or S substituted moieties.

5) Substitution on the homoserine lactone ring portion of the molecule. For example: addition of a sulfur group to produce a thiolactone.

6) Halogenated acyl furanones have been shown to act as blockers to homoserine lactone cognate receptor proteins.

7) Ring size of the acyl side chain varying heterocyclic moiety is variable. For example, 4-membered and 6-membered rings containing nitrogen (i.e., beta and delta lactams) are included.

Also, blocking analogs may bind to the HSL and scavenge it in free form from the environment. Such analogs have a binding site to OdDHL with a similar structure but greater affinity than the cognate binding protein, LasR.

The following are specifically preferred fluorinated and sulfur substituted blockers and analogs for use in the invention:

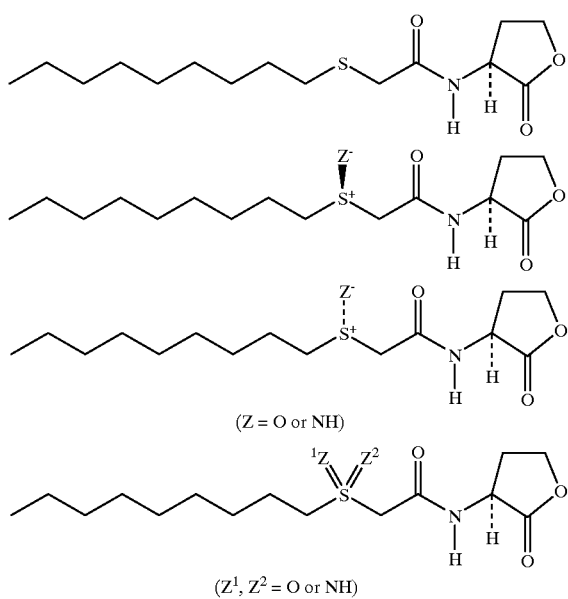

(Z = O or NH)

($Z^1$, $Z^2$ = O or NH)

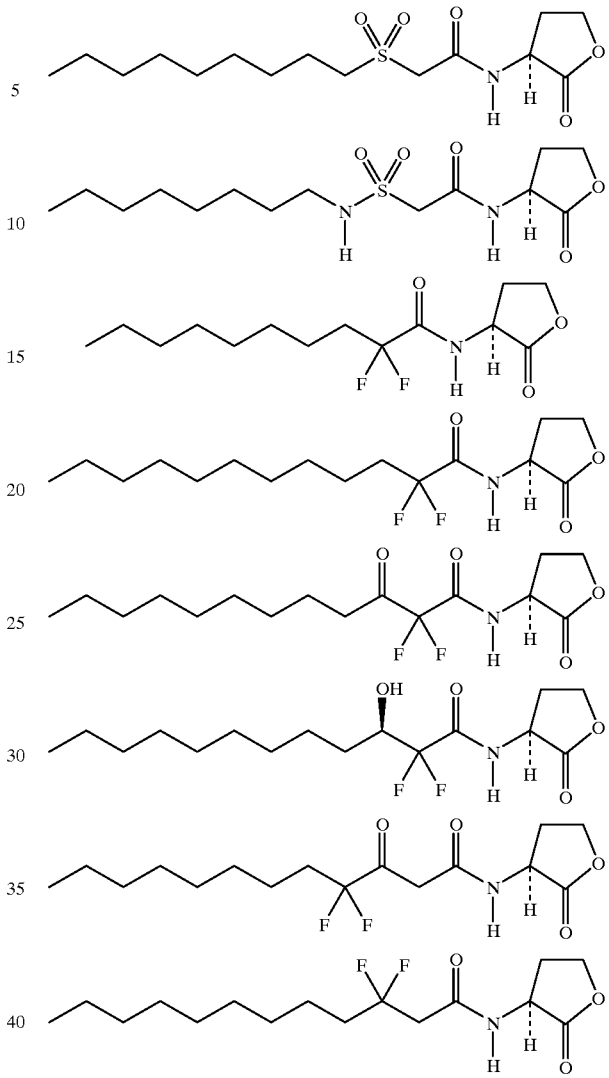

The present invention is suitable for biofilms originating from a single type of organism and for mixed biofilms. By "mixed biofilms" is meant biofilms created by more than one type of microorganism. Most preferably, it is envisioned that biofilms will be created by at least two organisms from the group consisting of bacteria, algae, fungi, and protozoa.

The effects of treating biofilms with homoserine lactones have been demonstrated with *Pseudomonas aeruginosa*. The HSLs have generally been isolated from a wide range of bacteria known to produce biofilms. Among these are the enterobacteria. The presence of the HSLs in a wide range of bacteria indicates that the compounds of the present invention can be used to effectively treat not only Pseudomonas sp. biofilms but also mixed biofilms containing Pseudomonas sp. and biofilms composed of bacteria other than *Pseudomonas aeruginosa*.

The following is a list of groups of Gram-Negative bacteria that have members which use homoserine lactones for cell-cell communication: anaerobic Gram Negative Straight, Curved and Helical Rods; Bacteroidaceae; The Rickettsias and Chlamydias; Dissimilatory Sulfate—or Sulfur-Reducing Bacteria; the Mycoplasmas; The mycobacteria; Budding and/or Appendaged Bacteria; Sheathed Bacteria; Nocardioforms; and Actinomycetes, for example. See *Bergey's Manual of Systematic Bacteriology*, First Ed., John G. Holt, Editor in Chief (1984), incorporated herein by reference.

Compositions of the present invention may be in the form of an aqueous solution or suspension containing a cleaning-effective or prevention effective amount of the active compound described above. The cleaning composition may be in the form of a spray, a dispensable liquid, or a toilet tank drop-in under-rim product for prevention, removal and cleaning of toilets and other wet or intermittently wet surfaces in domestic or industrial environments.

The compositions of the present invention preferably additionally comprise a surfactant selected from the group consisting of anionic, nonionic, amphoteric, biological surfactants and mixtures thereof. Most preferably, the surfactant is sodium dodecyl sulfate. The surfactant should be present in an amount at least 0.2% by weight, with a range of from 0.1% to 10% by weight.

One may wish to add other efficacious adjuvant compounds to the cleaning solution of the present invention. Most preferably, one may wish to add biocides, fungicides, antibiotics, and mixtures thereof to affect planktonics. One may also wish to add pH regulators, perfumes, dyes or colorants.

By "cleaning-effective" amount of active compound, it is meant an amount of the compound which is necessary to remove at least 10% of bacteria from a biofilm as determined by a reduction in numbers of bacteria within the biofilm when compared with a biofilm not exposed to the active compound.

By "prevention-effective" amount of active compound, it is meant an amount of compound that is effective to prevent normal. biofilm formation between normal cleaning times, most preferably preventing any biofilm build-up as determined by a statistically significant increase in the number of cells within a biofilm or upon a clean surface. Prevention of normal biofilm formation is determined by the ability to disperse a biofilm using surfactants and or detergents or other chemical treatments which will result in the removal of bacterial cells from a biofilm. To distinguish between normal biofilm formation and treatment with a prevention-effective amount of active compound, the treated biofilm must be shown to release 10% or more of its bacteria when compared with a similar biofilm that is not treated when both biofilms are exposed to surfactants and or detergents or other chemical treatments which will result in the removal of bacterial cells from a biofilm.

The application of OdDHL blocker to a solution should be in the concentration range of 10 nM to 100 uM and is preferably dissolved in a carrier containing a 3 to 1 ratio of water and ethanol or other organic solvent by volume. Further, the OdDHL blocker can be impregnated into a surface or other solid or semi-solid carrier which would release the blocker into the bulk environment at a concentration of 10 nM to 100 uM.

The application of BHL analog to a solution should be in the concentration range of 20 nM to 200 uM and is preferably dissolved in an aqueous carrier. Further, BHL or a BHL analog can be impregnated into a surface or other solid or semi-solid carrier which would release the compound into the bulk environment at a concentration of 20 nM to 200 uM.

Methods of the Present Invention

In another embodiment, the present invention is a method of biofilm removal or prevention. This method is suitable for both cleaning and preventing biofilm deposits and preventing biofilm deposits from accruing. It is envisioned that one would treat hard, rigid surfaces such as drain pipes, glazed ceramic, porcelain, glass, metal, wood, chrome, plastic, vinyl and formica or soft flexible surfaces such as shower curtains, upholstery, laundry and carpeting. It is also envisioned that both woven and non-woven and porous and non-porous surfaces would be suitable.

In one embodiment, the method comprises the steps of administering a cleaning-effective amount of the cleaning compound described above to a biofilm-containing surface or a surface that one wishes to remain biofilm-free. In another form of the present invention, one would administer an amount of the cleaning compound described above effective to prevent biofilm build-up or formation on a surface.

In particularly advantageous forms of the present invention, the method is used to remove biofilm on food preparation surfaces, such as kitchen counters, cutting boards, sinks, stoves, refrigerator surfaces, or on sponges and other cleaning implements, such as mops and wipes.

In another advantageous form of the present invention, the method is used to remove biofilm on bathroom surfaces, such as toilets, sinks, bathtubs, showers, and drains.

In another form, the present invention is used to remove biofilm on clothing and other woven and soft surfaces. This may be by means of a wipe, sponging or soaking method or by a laundering or detergent method. In another form of the present invention, the method is used to remove biofilm on floors and window surfaces, especially surfaces that are exposed to moisture, such as kitchen floor, shower stalls, and food production areas. In another form of the present invention, the method is used to remove biofilm in large-scale sanitation applications, such as food production machinery, processing areas and conduits that carry raw materials or finished products.

In other forms of the present invention, the method is used to prevent or remove biofilm as a dentifrice, a mouthwash, a compound for the treatment of dental caries, acne treatment, cleaning and disinfecting contact lenses, and medically implanted devices that are permanent such as an artificial heart valve or hip joint, and those that are not permanent such as indwelling catheters, pacemakers, surgical pins etc. The method is further used to prevent or remove biofilm in situations involving bacterial infection of a host, either human or animal, for example in a topical dressing for burn patients. An example of such a situation would be the infection by *P. aeruginosa* of superficial wounds such as are found in burn patients or in the lung of a cystic fibrosis patient.

In other forms, the present invention can be used to control or prevent the development of biofilm in the process of manufacturing integrated circuits, circuit boards or other electronic or microelectronic devices.

Methods to Verify the Suitability of Candidate Compounds

One wishing to practice the method of the present invention will evaluate candidate compounds for efficacy as OdDHL blockers or BHL analogs. The description below discloses a preferred method of evaluating candidate compounds and products containing the candidate compounds. In brief, one would first wish to grow biofilm in a controlled manner and observe the effect of candidate compounds on the biofilm.

Initial screening will be performed to examine the efficacy of potential cell communication blocking molecules to interfere with biofilm processes that are known to be responsive to regulation by homoserine lactones. These screens are based on information gathered through experimentation on the influence of the acyl homoserine lactone OdDHL on the development of *P. aeruginosa* biofilms. Four parameters have been developed which are sensitive to the presence of HSL compounds.

1. Biofilm average cell cluster depth: This parameter is a measure of the average thickness in microns of cell clusters in a biofilm. Depth measurements are performed microscopically, by measuring the maximum distance from the substratum to the apex of a biofilm cell cluster at the bulk water interface in a steady state biofilm for a minimum of 20 cell clusters. Previous measurements have shown that with *P. aeruginosa,* the average cell cluster depth is 102.3 um with a standard error of the mean of 20.5 um. When the gene responsible for the production of the homoserine lactone OdDHL is knocked out, the average cell cluster depth drops to only 22.8 um with a standard error of the mean of 10.0. When OdDHL is added back to the nutrient feed, the biofilm recovers its average cell cluster thickness of 100.1 um with a standard error of 25.2, demonstrating that the homoserine lactone is responsible for mediating biofilm cell cluster thickness.

2. Biofilm cell nearest neighbor analysis: This parameter is a measure of the average distance spacing between cells within a biofilm cell cluster or between cells at a substratum. Both measurements are influenced by the presence of the homoserine lactone OdDHL. The nearest neighbor analysis is performed by imaging 20 or more fields in a biofilm reactor and electronically determining the centroid of each cell. The relative distances from a marker cell to all other cells is computed and iterated for each cell in the population. The average nearest neighbor is then calculated. FIG. 1 shows results from a nearest neighbor analysis performed at the substratum for wild type *P. aeruginosa* (PAO1), and mutants knocked out in the ability to produce OdDHL and BHL (JP2), OdDHL (JP1), and BHL (PDO100). The bar graph demonstrates that the wild type average nearest neighbor is over 9 um in distance compared to the OdDHL knockout which is under 4 um. When OdDHL is added to the nutrient feed of the mutant defective in the production of that HSL, the average nearest neighbor increases to just over 9 um in distance. This demonstrates the influence of cell-cell communication on the arrangement of bacteria in biofilm cell clusters.

3. Effect of detergent on Biofilm dispersion: The detergent SDS has been shown to have no effect on the integrity of cell clusters formed by wild type *P. aeruginosa*. It has been shown previously (Davies, Doctoral Thesis, Montana State University, 1996) that matrix polymer, specifically alginate, prevents the dissolution of *P. aeruginosa* cell clusters treated with 0..2% SDS. However, when cell clusters are formed in the absence of alginate they are completely disrupted in under 30 minutes (FIGS. 2a, 2b, 2c and 2d). By microscopic examination of cell cluster thickness before and after treatment with SDS or by capturing effluent samples following similar treatment, a quantitative evaluation of the effect of agents capable of blocking the production of detergent resistant matrix material can be made.

Figure 3A:
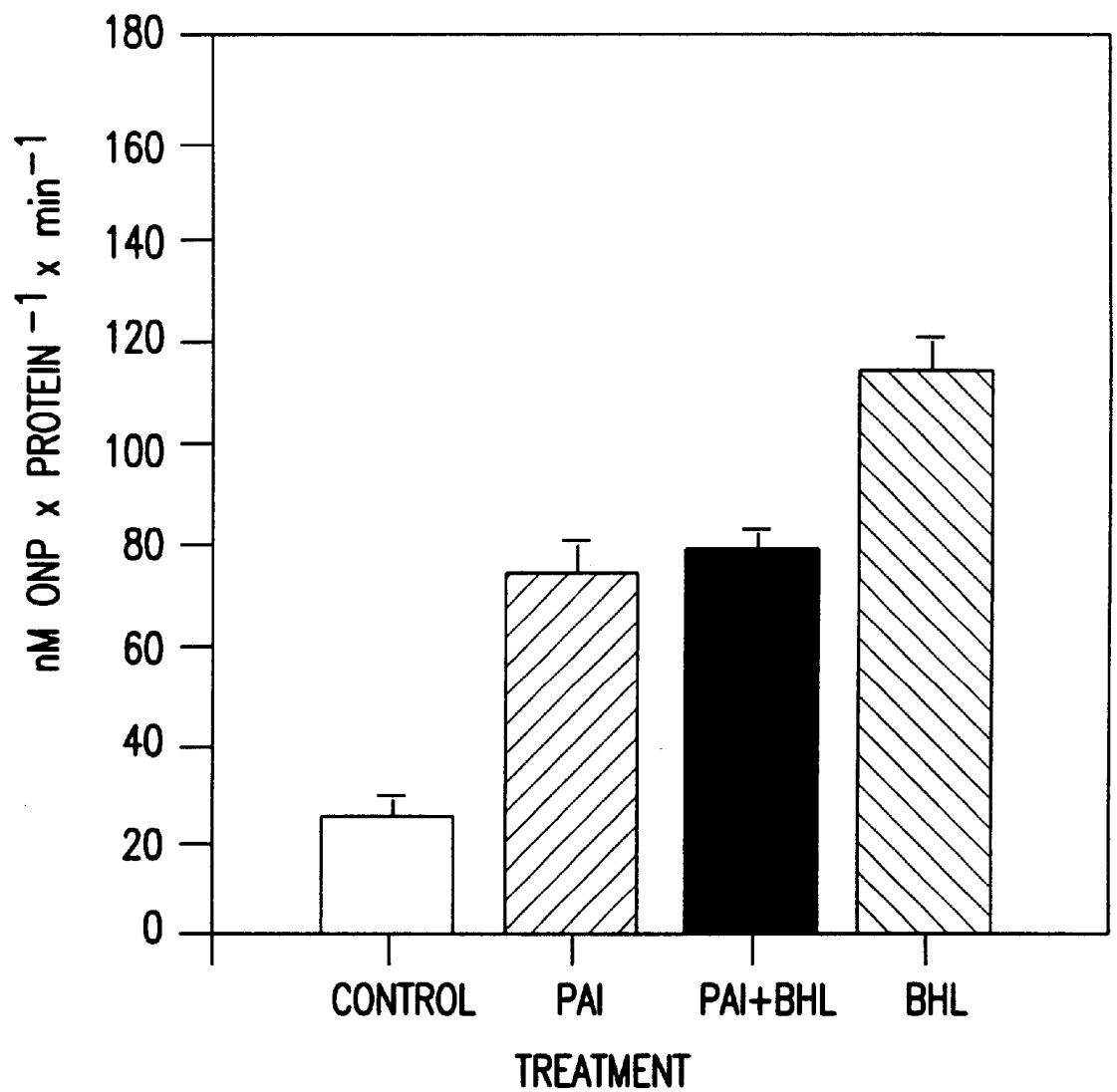
FIGS. 3a and 3b are alginate promoter studies which show the activity of the alginate promoters algC, and algD. Cultures of *P. aeruginosa* strain 8830 were grown for 48 hours in batch culture flasks containing EPRI medium. Test flasks were amended by either 10 uM OdDHL (PAI), 20 uM BHL (butyryl-L-homoserine lactone) or both (PAI+BHL). Following incubation, cells were harvested and promoter activity was measured as specific activity of the beta-galactosidase reporter enzyme as normalized to cell protein. The top graph (FIG. 3a) shows the results for algC specific reporter activity. The bottom graph (FIG. 3b) shows the results for algD specific reporter activity.
Figure 3B:
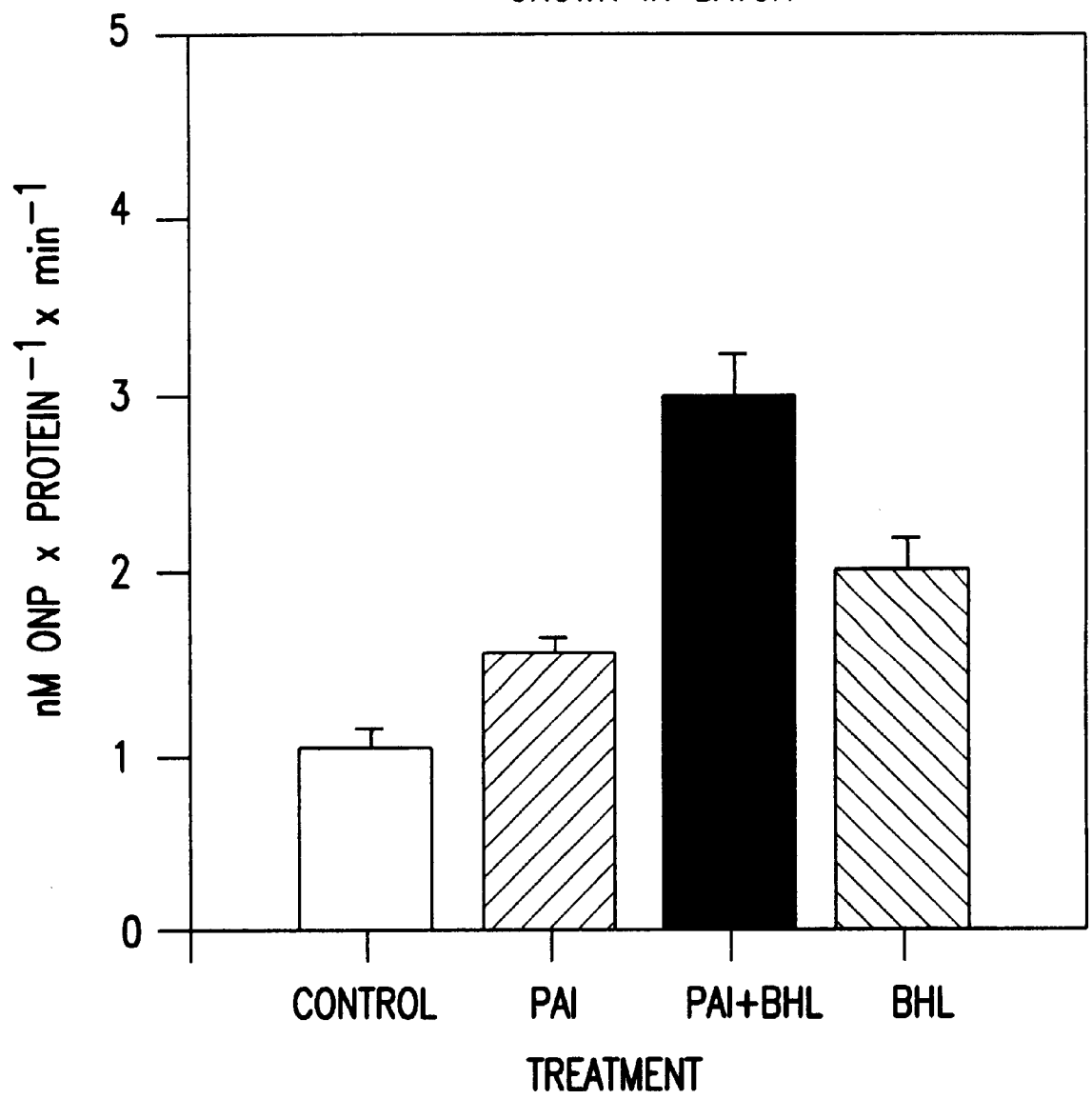
Figure 4A:
FIGS. 4a, 4b, 4c, 4d, 4e and 4f is a comparison study which shows the effect of 0.2% SDS on wild-type *P. aeruginosa* PAO1. The bacteria were grown in EPRI medium in continuous culture for 10 days (a,d). Following the incubation period, 0.2% SDS was added to the reactor and flow was halted for 30 minutes (b,e). Following incubation with SDS, flow was reinitiated (c,f). The left panel shows that during such treatment, wild-type PAO1 (untreated) shows no indication of cell dispersion (a,b,c). The right panel shows that when the wild-type strain is cultured in the presence of 20 uM OdDHL analog (N-(2,2-difluorodecanoyl-L-homoserine lactone), the cell cluster disperses completely following reinitiation of flow (d,e,f).
Figure 4D:
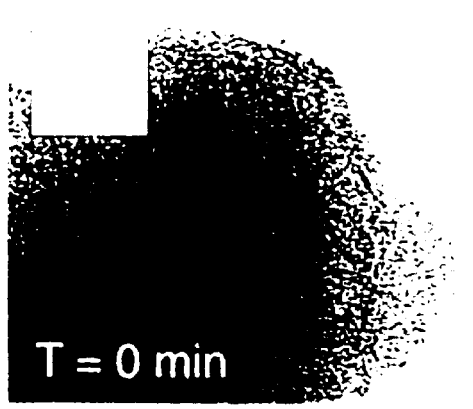
Figure 4B:
Figure 4E:
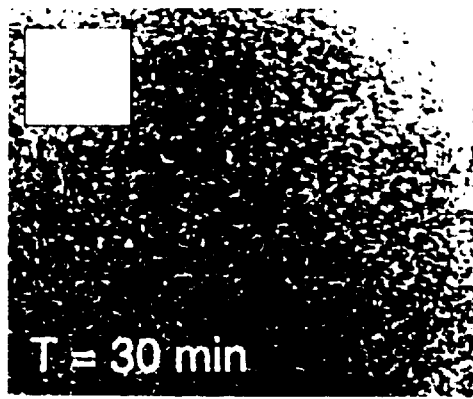
Figure 4C:
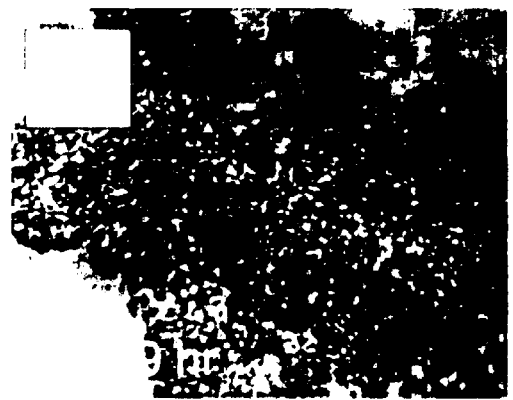
Figure 4F:

4. Alginate promoter reporter activity: The alginate promoters algC and algD have been shown to be sensitive to the presence of both OdDHL and BHL (FIGS. 3a and 3b). Alginate is a common matrix material in biofilms, and is not exclusive to *P. aeruginosa*. The sensitivity of *P. aeruginosa* to HSL activity provides a rapid assay for HSLs that is sensitive and quantitative. The responsiveness of the specific biofilm genes algc and algD to HSL activity allows assays to be performed in liquid or on semi solid medium. This provides the opportunity to perform rapid screening of test molecules for their effect on alginate production.

a. Method to crow biofilm in 'slide reactor'.

An autoclavable petri dish is equipped with an inlet tube set into the upper portion of the lid and an outflow tube set within the edge of the lower portion. A microscopy slide is placed inside the Petri dish such that the inlet tube is above the upper portion of the slide and the outflow tube at the middle to the lower edge. (The Petri dish and attached tubing are autoclaved and not opened until the biofilm is harvested.) While horizontal, a small amount (e.g. 3 ml) of a suspension of biofilm forming microorganisms (e.g. *Pseudomonas aeruginosa*) is injected through the wall of the tubing so that it drips onto the microscopy slide and covers the slide. After a suitable time, e.g. 1 hour, the Petri dish is raised into a slanted position, so that the inlet tube is at the top and the outflow at the bottom with the microscope slide vertically placed between the two. The slide drains through the outflow. After a suitable drying time (preferably 10 to 30 minutes) the inlet tube is connected via a pump to a reservoir of dilute media, e.g. Tryptic Soy Broth at 1/100 the normal strength. The media is pumped at a slow rate so that 1 drop is dispensed onto the top of the slide approximately every 10 seconds. The drop will run down the slide and exit via the outflow. A biofilm will form on the slide and will be visible after several days. A good time to use the biofilm for testing is when it reaches a total density of $10^8$ to $10^9$ cells which usually happens after 5–6 days. Several such drip reactors may be set up in a parallel fashion.

b. Determining whether candidate compounds are BHL analogs by analyzing whether the compounds remove biofilm buildup from surfaces (Laboratory Method).

Once biofilm has formed on the slides, three or more slides may be used for treatment, although at least three should be left as untreated controls. Treatment may be done within the Petri dish by switching the inflowing medium to the treatment solution to be tested. The treatment solution will contain a candidate compound or compounds.

The treatment solution initially will contain a BHL analog at the highest recommended concentration. The biofilm will be exposed to the treatment for a time period which will depend on the nature of the compound and the anticipated conditions of treatment by the consumer. At the conclusion of the treatment period the biofilms on the surface are rinsed with sterile water or buffer solution to remove loose cells. The treatment may be repeated using a formulation containing surfactants, digestive enzymes or other adjuvants which might aid in the removal and or disinfection of biofilms in combination with a BHL analog. Any active compounds within the formulation would be neutralized in combination with or following the rinse step. Thus, the biofilm is exposed to the treatment and the treatment should be continued for a reasonable time, depending on the nature of the compound. At the conclusion of the experiment all biofilms are harvested and rinsed with sterile water to remove loose cells. A neutralizing step to arrest the effect of the product may be in order at this point.

The slides are then scraped into 10 ml of sterile water or buffer solution and homogenized gently to free the cells from the biofilm matrix. After serially diluting an aliquot and plating on a suitable medium (e.g. R2A agar) the cells are enumerated using the plate count technique or other suitable procedure.

Additional tests which show the effect of the product on the biofilm should include total protein and carbohydrate analyses. If the cells are Pseudomonads, determination of uronic acid (alginate) is advisable. By comparing these data with those obtained from the untreated biofilm the effect of the treatment may be determined.

Instead of these drip reactors, biofilms may be grown in an Annular Reactor ("Rototorque") or Rotating Disk Reactor (Biosurface Technologies, Bozeman, Mont.). Conditions may be varied to resemble the nature of the product application.

The effectiveness of compounds to kill cells previously protected within a biofilm can also be shown by administering a biocide of choice together with the candidate compound. Cells will be killed faster and at lower biocide concentrations than those needed for combating biofilm contamination.

Treatments under realistic conditions may be carried out within consumer homes or any location targeted by the compound. One would first wish to combine the candidate compound with materials appropriate for a particular cleaning or preventative product. (See Examples below for exemplary products.) Surfaces may be partially treated with the respective product, cells may be scraped from untreated and treated surfaces and assayed as above. It is important to include a rinse and/or agitation step following the treatment to remove the loosened biofilm from the respective surfaces.

c. Determining whether a candidate compound is an OdDHL blocker by analyzing whether the compound prevents biofilm formation.

Cells are allowed to attach to surfaces within slide reactors, Annular Reactors, etc., as described above. The candidate compound, in this case, is applied together with the medium, while the biofilm is growing (product is withheld from the controls). After a set time, usually 4–6 days, the slides are treated as described above. While cells may have attached to the product treated surfaces, they will not have formed biofilm, i.e. the carbohydrate and alginate component of the treated surfaces will be lower than those for the control. There may also be fewer cells than on the control surfaces and these unprotected cells will readily succumb to biocide action.

Treatments under realistic conditions will show that biofilm fails to grow normally on surfaces exposed to products containing OdDHL blockers. In one such application, a product is continuously dispensed into the toilet tank and with every flush contacts the porcelain surfaces of a previously cleaned toilet. (The addition of BHL or a BHL analog may be used as a second active compound to disperse previously existing biofilm.) Biofilm build-up will be prevented in this way, which will also eliminate biofilm dependent lime-scale formation and discoloration and biofilm associated odors. In another example, OdDHL blockers and BHL or a BHL analog are allowed to circulate within cooling coils of cooling towers or heat exchangers. Both products together break up existing biofilm and prevent new biofilm formation.

The following examples are presented to illustrate various aspects of the invention but are not considered to be limiting on the scope of the invention.

EXAMPLES

Example 1

The most unequivocal experimental design, to determine the role of HSL signal molecules on the formation of biofilms by cells of *P. aeruginosa*, was to use direct microscopic methods to monitor biofilm formation by cells of HSL negative mutants. For this reason planktonic cells of a wild-type strain (PAO1), and of three mutants incapable of synthesizing specific HSLs, were introduced into flow cells, and adhesion and biofilm formation were monitored by means of confocal scanning laser microscopy (CSLM). Using these techniques, it is possible to monitor the development of live biofilms of the strains of interest.

Bacteria and media. The Bacteria strains used in this study are listed in Table 1. All experiments were performed using a defined culture medium containing the following, in grams per liter: sodium lactate, 0.05; sodium succinate, 0.05; ammonium nitrate, 0.05; $KH_2PO_4$, 0.19; $K_2HOP_4$, 0.63; Hutner Salts (Cohen-Bazire, 1957), 0.01; glucose, 1.0; and L-histidine, 0.01. Solid R2A medium was used for the enumeration of bacteria from continuous culture experiments. $HgCl_2$ (7.5 ug/ml in continuous culture and 15 ug/ml on solid medium) and tetracycline 25 ug/ml in continuous culture and 50 ug/ml on solid medium) were used to ensure plasmid and transposon maintenance during experiments.

TABLE 1

Bacterial strains and plasmids used in experiments

| P. aeruginosa | Relevant Characteristics | Source/Reference |
| --- | --- | --- |
| PAO1 | wild type Cell-cell communication unaltered | [1]Holloway (1955) |
| PAO-JP1 | las::tet strain PAO1 derivative Does not produce OdDHL | [2]Pearson, et al. (1997) |
| PDO100 | rhlI::Tn501-2 stain PAO1 derivative Does not produce BHL | [3]Brint and Ohman (1995) |
| PAO-JP2 | lasI::tet, rlhlITb501-2 PAO1 derivative Does not produce OdDHL and BHL | [4]Pearson, et al. (1997) |

[1]Bacteriol. Rev. 33: 419–443 (1955)
[2]J. Bacteriol. 179: (1997)
[3]J. Bacteriol. 177: 7155–7163 (1995)
[4]J. Bacteriol. 179: (1997)

Continuous culture studies. A continuous culture apparatus was developed to observe the growth and development of biofilms attached to a glass substratum. The apparatus was configured as a once through flow cell system. The influent defined culture medium was retained in a four liter glass reservoir. Medium from the influent reservoir was pumped through silicone tubing via a Masterflex pump to an aeration flask sparged with a filtered air source. The aerated medium was pumped to a flat plate flow cell using a Masterflex 8 roller-head peristaltic pump at a flow rate of 0.13 ml min$^{-1}$. The flow cell was constructed of polycarbonate having a depth of 1.0 mm, a width of 1.4 cm, and a length of 4.0 cm, the upper face was capped with a glass coverslip. The glass coverslip was used as a substratum for bacterial attachment and biofilm development because it is relatively inert material and its transparency allowed improved visual observation. Flow through the cell was laminar, having a Reynolds number of 0.17, with a fluid residence time of 0.43 minutes. The flow cell was sealed to prevent contamination and affixed to the stage of an Olympus BH2 microscope. Medium leaving the flow cell was pumped to an effluent reservoir via silicone tubing. The entire system was closed to the outside environment but maintained in equilibrium with atmospheric pressure by a 0.2 $\mu$m pore size gas permeable filter fitted to each flask.

Log phase *P. aeruginosa* were inoculated through a septum approximately 1 cm upstream from the flow cell while flow was maintained. Bacteria were allowed to attach to and grow on the surfaces of the system downstream from the site of inoculation over a period of 24 hours. Flow through the system was then increased to remove any bacteria attached to the inside surface of the coverslip (as determined by microscopy). Bacteria shed from biofilm upstream from the flow cell were then allowed to recolonize the surfaces of the flow cell under conditions of normal flow. Cells attached to the inner surface of the glass coverslip were viewed by transmitted light using a 40×magnification A40PL and a 50×magnification ULWD MSPlan long working distance Olympus objective lens to detect total cells. All images were stored as separate files for subsequent retrieval and analysis.

Biofilm Development and Measurement

Modified Lowry protein assay. The Lowery protein assay was performed on samples as described previously (Peterson, 1977) and analyzed with a Milton Roy Spectronic 601 spectrophotometer.

Uronic acid assay. Total uronic acids were measured in thawed samples of scraped biofilm and whole culture following the method of Kintner and Van Buren (1982) using a Milton Roy Spectronic 601 spectrophotometer. A total polysaccharide assay and lipopolysaccharide analysis were also performed.

Biofilm architecture. The growth and development of biofilms has been shown to result in the production of specific architectural components (Costerton, et al., Ann. Rev. Microbiol., 49: 711–745, 1995). It is shown that biofilm architecture is influenced by cell-cell communication.

Biofilms of P. aeruginosa PAO1 were grown in a bioreactor and examined by microscopy coupled with image analysis. Development of the wild-type organism into a mature biofilm over a two week period, resulted in cell clusters ranging in size from 40–120 μm with an average thickness of 102.3 μm (sd=20.5 n=20). These cell clusters were shown to contain water channels, have few cells attached to the substratum and were composed of bacteria well separated from one another. These cell clusters were then compared with those developed by P. aeruginosa which were defective in the ability to synthesize the homoserine lactone molecules OdDHL, BHL or both. Under the same experimental conditions, cell clusters developed by the mutant strain P. aeruginosa JP2 which lacked the ability to synthesize either of the homoserine lactones, the architectural components of the wild-type organism were found to be missing. The clusters ranged in size from 20–40 μm with an average thickness of 23.5 μm sd=9.8 n=20. Cells in these clusters were densely packed and did not develop water channels. When P. aeruginosa PAO-JP1 detectable only in OdDHL were grown under similar conditions, they were shown to produce clusters similar in size to the P. aeruginosa POA-JP2 mutant (average thickness=22.8um, sd=10.0, n=20), but containing large spaces devoid of cells in the cluster interior. The mutants defective only in BHL synthesis produced cell clusters that were similar to the wild-type organism (average thickness=100.1 um, sd=25.2, n=20).

Example 2

To confirm that HSL was responsible for the architectural differences noted between wild-type and mutant biofilms, an experiment was performed to demonstrate that addition of filterable material collected from medium in which the wild-type organism had grown would recover the wild-type architecture in the double mutant, P. aeruginosa PAO-JP2. When the double mutant was thus grown as a biofilm, it developed an intermediate from between the wild-type and the untreated double mutant. The interior of the cell clusters appeared similar to the untreated P. aeruginosa PAO-JP2 and the exterior of the cell clusters appeared similar to the wild-type organism.

This experiment was repeated, culturing the double mutant using a concentration of 10 μM OdDHL in fresh medium. This resulted in recovery of the intermediary phenotype as was observed when the cells were grown in the presence of spent medium. These results indicated that biofilm architecture P. aeruginosa PAO1 biofilms is conferred by cell-cell communication. Accordingly, the inventors conclude that OdDHL is able to control this architectural development.

Biofilm matrix polymer. The architectural differences noted when comparing biofilms developed by wild-type and HSL mutant P. aeruginosa led us to predict that matrix polymer production and regulation are controlled by homoserine lactone. To test this theory, biofilm samples of P. aeruginosa PAO1 and P. aeruginosa PAO-P2 were cultured for two weeks in a biofilm reactor. When these cultures were analyzed for uronic acids production, the wild-type strain was shown to produce detectable levels, however, none were detectable in the double mutant (Table 2).

This result indicated that the strain P. aeruginosa PAO-JP2 does not produce detectable uronic acids in continuous culture. When this strain is cultured in spent medium from the wild-type, filtered and amended with glucose, the production of uronic acids was recovered. No uronic acids were detectable in the filtered medium from the wild-type organism. The uronic acids assay detects mannuronic acid which is found in alginate and certain forms of lipopolysaccharide (LPS). The results indicated that one or both of these compounds is under the regulation of OdDHL.

TABLE 2

Uronic Acids Production in P. aeruginosa PAO1 biofilms.

| Sample | Uronic Acids/Protein (ug/ug) |
|---|---|
| P. aeruginosa PAO1 | $3.97 \times 10^{-4}$ +/− $0.41 \times 10^{-4}$ |
| P. aeruginosa PAO-JP2 | ND[b] |
| Filtered medium | $1.62 \times 10^{-5}$ +/− $0.20 \times 10^{-5}$ |
| P. aeruginosa PAO-JP2[a] | ND[b] |

[a]Cells grown in filtered medium from P. aeruginosa PAO1 culture.
[b]Not Detectable.

It has been shown that in mucoid strains of P. aeruginosa, alginate lyase is capable of degrading extracellular alginate (Boyd, et al., Appl. Environ. Microbiol., 60: 2325–2359, 1994). Further studies by the inventors demonstrated that alginate lyase can degrade extracellular alginate when released artificially from P. aeruginosa strain 8830 in biofilms. Following the destruction of extracellular alginate, these bacteria can be completely dispersed through the addition of 0.2% sodium dodecyl sulfate (SDS) (Davies, Doctoral Thesis, Montana State University, 1996).

In the present experiment, treatment with the detergent was shown not to affect the biofilm in the absence of released alginate lyase. When P. aeruginosa PAO1 was treated with 0.2% SDS under similar experimental conditions, no dispersion or release of bacteria from the cell clusters was observed. When P. aeruginosa PAO-JP2 was treated with SDS in the same manner, the cell clusters were shown to disperse completely, showing a similar effect to what had been seen for P. aeruginosa strain 8830 following degradation of alginate. This experiment was repeated using the single HSL mutant strain P. aeruginosa PAO-JP1, which was shown to disperse completely following the addition of SDS. When P. aeruginosa PAO-JP1 was grown in the presence of 10 μM OdDHL, treatment with 0.2% SDS did not disperse bacteria in the cell clusters. The presence of the homoserine lactone, therefore, was shown to be responsible for resistance to dispersion by detergent action.

Biofilm dispersion. OdDHL has been shown to regulate the development of biofilm architecture and resistance to dispersion by detergent. It appears that BHL is also involved with natural dispersion of bacteria in biofilms. When the OdDHL mutant P. aeruginosa PAO-JP1 was grown as a biofilm, large void spaces were detected in the interior of the cell clusters. During the growth phase of cell clusters of P. aeruginosa PAO-JP1, central void spaces developed after 7 days in clusters greater than 50 μm in diameter. These voids had previously been occupied by bacteria that were observed to become actively motile and eventually swim away from the cluster interior via a break through the cluster wall. It was postulated that the presence of such central voids, which were not detected in cell clusters formed by P. aeruginosa PAO-JP2 or P. aeruginosa PDO100, indicated the possibility that BHL is responsible for the release of enzymes which can degrade matrix polymer material.

This hypothesis was investigated by growing biofilms of P. aeruginosa PDO100 and adding BHL to the influent medium at a concentration of 20 μM after 7 days growth. Following the addition of BHL for 24 hours, no observable effect was detected. Medium flow was then shut off for a period of 16 hours, at which time, significant detachment began to occur and continue for a period of three hours. When P. aeruginosa PDO100 was grown in the absence of BHL, medium flow was turned off after 7 days. Following cessation of flow, no dispersion of cell clusters was observed over the duration of the observation period of 96 hours.

Example 3
Use of OdDHL Analog to Prevent Normal Biofilm Development

As a typical embodiment of the invention, an OdDHL blocking agent was used to demonstrate that normal biofilm development could be disrupted and the biofilm dispersed following the addition of 0.2% SDS. An analog of OdDHL, N-(2,2-difluorodecanoyl)-L-homoserine lactone was dissolved in 25% ethanol, 75% water by volume and added at a final concentration of 10 uM to growing biofilm cultures of P. aeruginosa PAO1 wild-type. Following 10 days incubation, the biofilm was analyzed for cell to cell distances, cell cluster thickness and response to treatment with 0.2% SDS. It was shown after 10 days incubation that the average cell to cell distance was less than 4 um and was not significantly different from that observed with the OdDHL knockout mutant P. aeruginosa PAO-JP1. The cell cluster average thickness was under 20 um and was not significantly different from the OdDHL knockout P. aeruginosa PAO-JP1. Finally, when treated with 0.2% SDS by weight, the treated biofilm was disrupted and dispersed within 30 minutes (FIGS. 5a to 5f). These results are similar to what has been observed with the OdDHL knockout, but significantly different from the untreated P. aeruginosa PAO1 wild-type. These results demonstrate that the addition of an OdDHL blocking agent can prevent normal biofilm development of P. aeruginosa PAO1 wild-type when that organism is grown in continuous culture in the presence of 10 uM of the blocking agent over a period of 10 days.

Example 4
Examples of Preferred Embodiments

Shown below are formulations of products comprising compounds of the present invention.

i. Liquid General Purpose Heavy Duty Cleaner

| | |
|---|---|
| calsuds 81N Concentrate | 2.0–4.0% |
| tetrapotassium pyrophosphate | 5.0–10.0% |
| sodium xylene sulfonate (40%) | 7.5–12.5% |
| BHL analog | 2–5 ppm |
| water to 100% | |

A product of this type can be used in diluted form to wash walls, floors, tiles and windows to remove heavy grease and soils and can be used as an aid to heavy duty laundering.

ii. Liquid low foam rug cleaner

| | |
|---|---|
| Dowfax 2A-1 Surfactant | 5.0–9.0% |
| triethanolamine | 8.0–12.0% |
| Dowanol PM Glycol Ether | 3.5–5.0% |
| potassium oleate | 76–80% |
| BHL analog | 2–5 ppm |
| water to 100% | | iii. Toilet Bowl and Metal Cleaner

| | |
|---|---|
| veegum stabilizer | 0.6–1.0% |
| xanthan gum | 0.2–0.6% |
| tetrasodium EDTA | 0.8–1.1% |
| 1-hydroxyethyl-2-caprylimidazoline | 0.6–1.2% |
| phosphoric acid (86%) | 12.0–20.0% |
| kaolin | 8.0–12.0% |
| BHL analog | 2–5 ppm |
| water to 100% | | vi. Liquid dairy cleaner

| | |
|---|---|
| phosphoric acid (85%) | 30.0–40.0% |
| hydrochloric acid (20) | 15.0–20.0% |
| Petro BA Surfatrope (50% liquid) | 1–3.5% |
| BHL analog | 2–5 ppm |
| OdDHL blocker | 2–5 ppm |
| water to 100% | | v. Cleaner and germicide for kitchen implements, toys, medical instruments, etc.

| | |
|---|---|
| Barquat 4250-Z sensitizer | 4.0–6.0% |
| sodium carbonate | 1.0–4.0% |
| sodium citrate | 1.0–3.0% |
| Tergitol TP-9 Surfactant | 1.0–4.0% |
| BHL analogs | 2–5 ppm |
| water to 100% | | vi. Treatment for sprayer in cafeterias and hospital kitchens and catering establishments:
Add concentrate to water to final concentration of 1–6

| | |
|---|---|
| ppm concentrate: | 150–500 ppm OdDHL blockers |
| | 150–500 ppm BHL analog in water | vii. Radiator cleaner
Add OdDHL blocker and/or BHL analog to usual cleaning composition to final concentration of 2–5 ppm Adjust pH not to exceed 9.0

The invention has been described herein with reference to certain preferred embodiments. However, as obvious variations thereon will become apparent to those skilled in the art, the invention is not considered to be limited thereto.

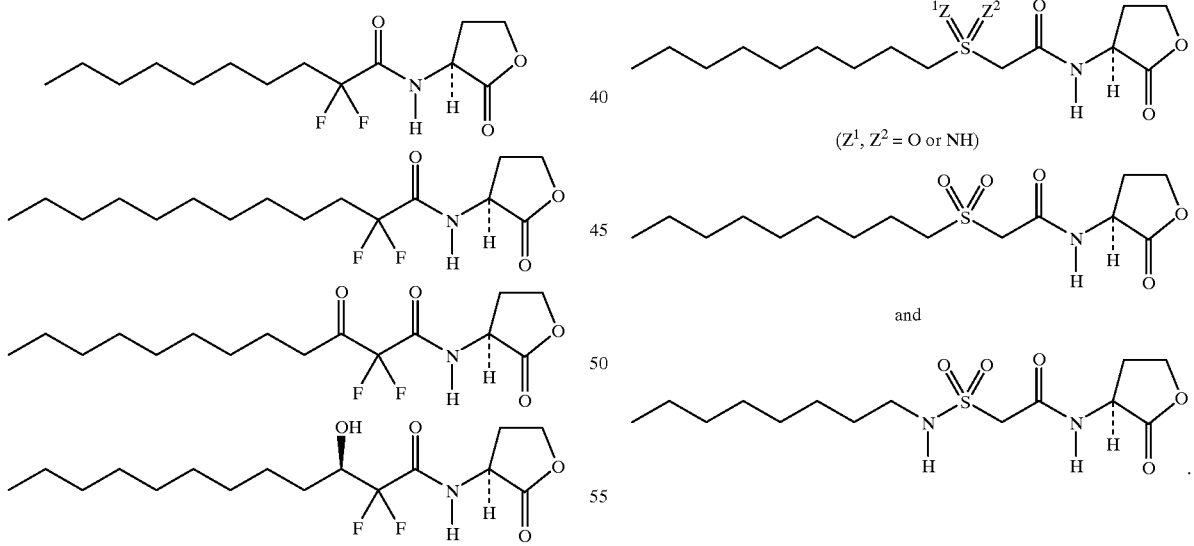

What is claimed is:

1. A biofilm removing or inhibiting composition comprising an amount of a mixture of analogs of butyryl L-homoserine lactone (BHL) and blockers of N-(3-oxododecanoly) L-homoserine lactone (OdDHL), and a vehicle or carrier, wherein the amount of the mixture is effective to remove or disrupt a bacterial biofilm or inhibit normal biofilm formation.

2. A biofilm removing or inhibiting composition comprising an amount of a compound selected from the group consisting of blockers of N-(3-oxododecanoly) L-homoserine lactone (OdDHL), and mixtures of blockers of OdDHL and analogs of butyryl L-homo-serine lactone (BHL), and a vehicle or carrier, wherein the amount of the compound is effective to remove or disrupt a bacterial biofilm or inhibit normal biofilm formation wherein the OdDHL blocker has the following structure:

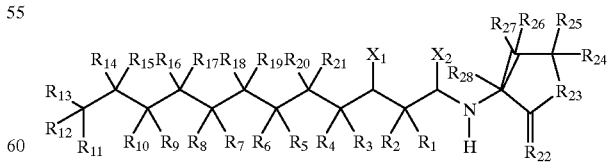

wherein
$R_1$–$R_{21}$ are selected from the group consisting of H, $C_1$–$C_4$ alkyl group, OH, $NH_2$, SH and a halogen, wherein the halogen is selected from the group consisting of fluorine, chlorine, bromine, and iodine;

$R_{22}$ and $R_{23}$ are selected from a halogen, H, S, N, NH, and O $R_{24}$–$R_{28}$ is H or a halogen, and $X_1$ and $X_2$ are selected from O, S, $H_2$ or any combination of H plus one halogen or two halogens when one or more R groups is substituted, and at least one of $R_1$–$R_{21}$ is a halogen, or the alkylene chain of the molecule contains a sulfur in the chain.

3. The composition of claim 2, wherein $R_{24}$ through $R_{28}$ are a H or halogen, and $R_{22}$–$R_{23}$ are a H.

4. The composition in claim 2 wherein one or more carbons forming the backbone of the molecule are substituted with S or S-substituted moieties.

5. The composition of claim 3 or 4 wherein the carbonyl group at $X_1$ and/or $X_2$ is substituted with $H_2$, H plus a halogen or two halogens.

6. A biofilm removing or inhibiting composition comprising an amount of a compound selected from the group consisting of analogs of butyryl L-homo-serine lactone (BHL), and mixtures of analogs of BHL and blockers of N-(3-oxododecanoly) L-homoserine lactone (OdDHL), and a vehicle or carrier, wherein the amount of the compound is effective to remove or disrupt a bacterial biofilm or inhibit normal biofilm formation wherein the analog of BHL has the following structure:

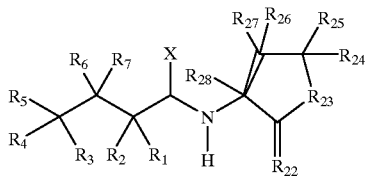

wherein $R_1$–$R_7$ are selected from the group consisting of H, $C_1$–$C_4$ alkyl group, OH, $NH_2$, SH and a halogen, wherein the halogen is selected from the group consisting of fluorine, chlorine, bromine, and iodine;

$R_{22}$ and $R_{23}$ are selected from H, S, N, NH, and O $R_{24}$–$R_{28}$ is H or a halogen, and X is selected from O, S, $H_2$ or any combination of H plus one halogen H plus OH or $NH_2$, a double bonded O, NH, S, or two halogens when one or more R groups is substituted, and at least one of $R_1$–$R_7$ is a halogen, or the alkylene chain of the molecule contains a sulfur in the chain.

7. The composition of claim 6, wherein $R_{22}$ is selected from H, S, O and NH and $R_{23}$ is selected from S, O, and N.

8. The composition of claim 6, wherein the acyl side chain contains one or more double bonds or triple bonds between carbon atoms within the acyl side chain.

9. The composition of claim 6 wherein X is selected from $H_2$, H plus a halogen, two halogens, H plus OH or $NH_2$, a double bonded O, NH or S.

10. A biofilm removing or inhibiting composition comprising an amount of a compound selected from the group consisting of blockers of N-(3-oxododecanoly) L-homoserine lactone (OdDHL) and analogs of butyryl L-homo-serine lactone (BHL), and mixtures thereof, and a vehicle or carrier, wherein the amount of the compound is effective to remove or disrupt a bacterial biofilm or inhibit normal biofilm formation, additionally comprising a surfactant selected from group consisting of anionic, nonionic, amphoteric, biological surfactants and mixtures thereof.

11. The composition of claim 10, wherein the surfactant is sodium dodecyl sulfate.

12. The composition of claim 2 in which the blocker is N-(2,2 difluorodecanoyl)-L-homoserine lactone.

13. The composition of claim 1 further comprising a compound selected from the group consisting of biocides, fungicides, antibiotics, and mixtures thereof.

14. A method of removing biofilm from a surface comprising the step of administering a cleaning-effective amount of the composition of claim 1 to a biofilm-containing surface.

15. A method of preventing biofilm formation on a surface comprising the step of administering an effective amount of the composition of claim 1 to a surface, wherein the amount is effective to prevent biofilm formation.

16. The method of claim 14 wherein the surface is a hard, rigid surface.

17. The method of claim 16 wherein the surface is selected from the group consisting of a drainpipe, glaze ceramic, porcelain, glass, metal, wood, chrome, plastic, vinyl, and formica.

18. The method of claim 14 wherein the surface is a soft, flexible surface.

19. The method of claim 18 wherein the surface is selected from the group consisting of shower curtains or liners, upholstery, laundry, and carpeting.

20. The method of claim 14 wherein the biofilm is produced by a bacteria of the class Pseudomonas.

21. The method of claim 20 wherein the bacteria is of the species *Pseudomonas aeuroginosa*.

22. The method of claim 14 wherein the biofilm is produced by an organism selected from the group consisting of bacteria, algae, fungi and protozoa.

23. A dentifrice comprising an effective amount of a composition of claim 1, wherein the amount is effective to either prevent or remove biofilm formation.

24. A mouthwash comprising an effective amount of a composition of claim 1, wherein the amount is effective to either prevent or remove biofilm formation.

25. A method for treatment of dental caries comprising administering an effective amount of a composition of claim 1, wherein the amount is effective to either prevent or remove biofilm formation.

26. A method of prevention of dental caries comprising administering an effective amount of a composition of claim 1, wherein the amount is effective to either prevent or remove biofilm formation.

27. A method of treatment of acne comprising topically administering an effective amount of a composition of claim 1, wherein the amount is effective to either prevent or remove biofilm formation.

28. A method of cleaning and disinfecting contact lenses comprising administering an effective amount of a composition of claim 1, wherein the amount is effective to either prevent or remove biofilm formation.

29. A microbial dispersing composition comprising an effective amount of composition of claim 1, wherein the amount is effective to either prevent or remove biofilm formation.

30. A biofilm removing or inhibiting composition comprising an amount of a compound selected from the group consisting of blockers of N-(3-oxododecanoly) L-homoserine lactone (OdDHL), analogs of butyryl L-homo-serine lactone (BHL), and mixtures thereof, and a vehicle or carrier, wherein the amount of the compound is effective to remove or disrupt a bacterial biofilm or inhibit normal biofilm formation, wherein the OdDHL blocker has the structure of formula I and the BHL analog has the structure of formula II:

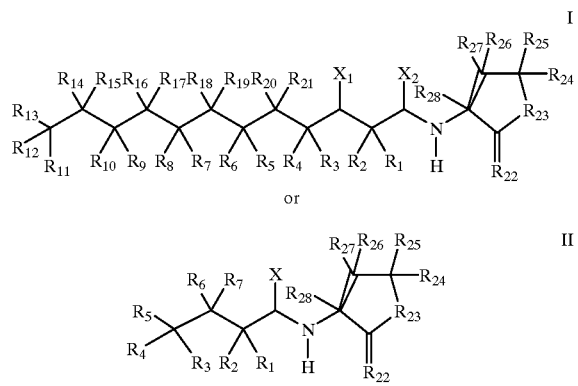

wherein

R$_1$–R$_{21}$ are selected from the group consisting of H, C$_1$–C$_4$ alkyl group, OH, NH$_2$, SH and a halogen, wherein the halogen is selected from the group consisting of fluorine, chlorine, bromine, and iodine;

R$_{22}$ and R$_{23}$ are selected from a halogen, H, S, N, NH, and O

R$_{24}$–R$_{28}$ is H or a halogen, and

X, X$_1$ and X$_2$ are selected from O, S, H$_2$ or any combination of H plus one halogen or two halogens when one or more R groups is substituted, provided that when the biofilm comprises an OdDHL blocker alone or a BHL analog alone, at least one of R$_1$–R$_{21}$ is a halogen, or the alkylene chain of the molecule contains a sulfur in the chain.

31. The composition of claim 1, wherein the OdDHL blocker is selected from the group consisting of:

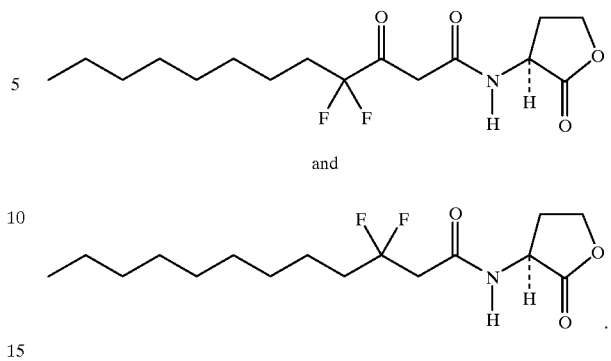

32. The composition of claim 1, wherein the OdDHL blocker is selected from the group consisting of: